(12) United States Patent
Qin et al.

(10) Patent No.: US 11,078,476 B2
(45) Date of Patent: Aug. 3, 2021

(54) METHODS AND KITS FOR EXTRACTING NUCLEIC ACIDS FROM PARAFFIN EMBEDDED SAMPLES

(71) Applicant: Fluidigm Corporation, South San Francisco, CA (US)

(72) Inventors: Jian Qin, Palo Alto, CA (US); Peilin Chen, Pleasant Hill, CA (US); Ramesh Ramakrishnan, San Jose, CA (US)

(73) Assignee: FLUIDIGM CORPORATION, South San Francisco, CA (US)

( * ) Notice: Subject to any disclaimer, the term of this patent is extended or adjusted under 35 U.S.C. 154(b) by 189 days.

(21) Appl. No.: 16/105,711

(22) Filed: Aug. 20, 2018

(65) Prior Publication Data

US 2019/0055540 A1 Feb. 21, 2019

Related U.S. Application Data

(60) Provisional application No. 62/547,548, filed on Aug. 18, 2017.

(51) Int. Cl.
 *C12N 15/10* (2006.01)
(52) U.S. Cl.
 CPC ..... *C12N 15/1003* (2013.01); *C12N 15/1013* (2013.01)
(58) Field of Classification Search
 None
 See application file for complete search history.

(56) References Cited

U.S. PATENT DOCUMENTS

| | | | |
|---|---|---|---|
| 5,155,018 | A | 10/1992 | Gillespie et al. |
| 5,876,924 | A | 3/1999 | Zhang et al. |
| 6,218,531 | B1 | 4/2001 | Ekenberg |
| 6,451,551 | B1 | 9/2002 | Zhan et al. |
| 6,469,159 | B1 | 10/2002 | Belly et al. |
| 6,632,598 | B1 | 10/2003 | Zhang et al. |
| 7,070,951 | B2 | 7/2006 | Zhang et al. |
| 7,527,979 | B2 | 5/2009 | Haik |
| 8,188,265 | B2 | 5/2012 | Costa et al. |
| 8,828,664 | B2 | 9/2014 | Fekete et al. |
| 9,097,628 | B2 | 8/2015 | Schlumpberger |
| 9,422,542 | B2 | 8/2016 | Holländer |
| 9,458,494 | B2 | 10/2016 | Mueller et al. |
| 2006/0252025 | A1 | 11/2006 | Nitta et al. |
| 2013/0280787 | A1 | 10/2013 | Mueller et al. |
| 2015/0004675 | A1 | 1/2015 | Hucklenbroich et al. |

FOREIGN PATENT DOCUMENTS

| | | |
|---|---|---|
| EP | 2395082 A1 | 12/2011 |
| EP | 2468862 A1 | 6/2012 |
| WO | 2011104027 A1 | 9/2011 |
| WO | 2013083260 A1 | 6/2013 |

OTHER PUBLICATIONS

Adams, N. et al. "Comparison of Three Magnetic Bead Surface Functionalities for RNA Extraction and Detection." *ACS Applied Materials & Interfaces*, vol. 7, Issue 11. Published Feb. 2015. pp. 6062-6069.
Smith, K. et al. "Comparison of Commercial DNA Extraction Kits for Extraction of Bacterial Genomic DNA from Whole-Blood Samples." *Journal of Clinical Microbiology*, Issue 41, No. 6. Published Jun. 2003. pp. 2440-2443.
Miszczak, F. et al. "Evaluation of Two Magnetic-Bead-Based Viral Nucleic Acid Purification Kits and Three Real-Time Reverse Transcription-PCR Reagent Systems in Two TaqMan Assays for Equine Arteritis Virus Detection in Semen." *Journal of Clinical Microbiology*, vol. 49, Issue 11. Published Nov. 2011. pp. 3694-3696.
Yang, G. et al. "Comparison of Commercial Systems for Extraction of Nucleic Acids From DNA/RNA Respiratory Pathogens." *Journal of Virological Methods*, vol. 171, Issue 1. Published Jan. 2011. pp. 195-199.
Fluidigm, "Advanta FFPE RNA Extraction Kit" PN 101-6554 A4 Protocol, Apr. 2018, 13 pages.

*Primary Examiner* — James Martinell
(74) *Attorney, Agent, or Firm* — Kilpatrick Townsend & Stockton LLP

(57) ABSTRACT

This invention provides a technology for isolating nucleic acids from wax-embedded samples that is superior to the current state of the art. Standard protocols with this objective typically comprise dissolving the wax-embedded sample in an organic solvent, extracting nucleic acids from the organic solvent into an aqueous buffer, and isolating the nucleic acids from the aqueous buffer. The technology described here includes using hexadecane as the solvent to dissolve the sample, precipitating and washing the extracted nucleic acids, and dissolving the nucleic acids in a lysis buffer that includes NP40 and SDS. By implementing the reagents and techniques described in this disclosure, the user can obtain a product that has better yield, less degradation, and contains more unique mRNA transcripts for subsequent sequencing and analysis.

17 Claims, 12 Drawing Sheets

Workflow of DNA+RNA Extraction from FFPE Biological Sample

Workflow of RNA Extraction from FFPE Biological Sample

| SDS concentration in lysis reaction | 0.0% | 0.2% | 0.4% | 0.6% | 0.8% | 1.0% |
|---|---|---|---|---|---|---|
| Nanodrop (ng/ul) | 31.2 | 29.0 | 29.6 | 29.6 | 29.2 | 27.5 |
| qPCR (ng/ul) | 21.8 | 21.3 | 23.0 | 23.2 | 23.1 | 26.0 |

| RNA Extraction Kit | Total Assays Detected Ct<28 | % | Total Assays Detected Cq<22 | % |
|---|---|---|---|---|
| Commercial kit #2 | 145 | 85.3% | 78 | 45.9% |
| Commercial kit #1 | 146 | 85.9% | 80 | 47.1% |
| Commercial kit #3 | 141 | 82.9% | 74 | 43.5% |
| Present kit | 156 | 91.8% | 104 | 61.2% |

| Operator | Minimum Yield (ng/uL) | Result |
|---|---|---|
| 1 | 30.4 | Pass |
| 2 | 60.0 | Pass |

|  | DV200 | | | | Result |
|---|---|---|---|---|---|
|  | Fluidigm | | Qiagen | | |
|  | Operator 1 | Operator 2 | Operator 1 | Operator 2 | |
| t-test p-value | 1.60E-11 | 2.20E-16 | 1 | 1 | Pass |
| WSR p-value | 7.67E-08 | 1.82E-12 | 1 | 1 | Pass |

| | Cq < 22 | | | | |
|---|---|---|---|---|---|
| | Fluidigm | | Qiagen | | Result |
| | Operator 1 | Operator 2 | Operator 1 | Operator 2 | |
| t-test p-value | 1.06E-09 | 9.92E-13 | 1 | 1 | Pass |
| WSR p-value | 4.53E-09 | 3.00E-11 | 1 | 1 | Pass |

| | Cq < 28 | | | | |
|---|---|---|---|---|---|
| | Fluidigm | | Qiagen | | Result |
| | Operator 1 | Operator 2 | Operator 1 | Operator 2 | |
| t-test p-value | 5.26e-06 | 3.029e-11 | 1 | 1 | Pass |
| WSR p-value | 2.317e-07 | 2.327e-08 | 1 | 1 | Pass |

METHODS AND KITS FOR EXTRACTING NUCLEIC ACIDS FROM PARAFFIN EMBEDDED SAMPLES

REFERENCE TO RELATED APPLICATIONS

This application claims the priority benefit of U.S. provisional application 62/547,548, filed Aug. 18, 2017. The priority application is hereby incorporated herein in its entirety for all purposes.

FIELD OF THE INVENTION

The invention relates to methods and kits for the extraction of nucleic acids from biological samples and finds application in the fields of genetics and medicine. The methods and kits described below are useful in extracting nucleic acids from biological samples for subsequent analysis including, but not limited to, nucleic acid sequencing and gene expression analysis in cell and/or tissue populations.

BACKGROUND

While formalin-fixed, paraffin-embedded (FFPE) tissue samples are a valuable source to our understanding of the genetic basis of certain diseases, DNA and RNA extraction from the FFPE samples has been challenging. The extraction, enrichment, and isolation of nucleic acids from FFPE samples is a complicated process that often requires the use of toxic organic solvents, prolonged periods of protease digestion, exposure to high temperature, and the use of high salt solutions Xylene, a toxic chemical, is commonly used to deparaffinize FFPE samples for DNA and RNA extraction. Deparaffinized tissues, after numerous washes to remove xylene, are normally digested with proteases and the nucleic acids are isolated using, for example, the phenol-chloroform method. In addition to the multistep process, the nucleic acids in the FFPE samples are often chemically modified and fragmented, thus the yield of the extracted nucleic acids from these samples is often low. Better methods are needed for extracting nucleic acids from wax-embedded biological samples.

SUMMARY OF THE INVENTION

This invention provides technology for isolating nucleic acids from wax-embedded samples that is superior to the state of the art at the time this disclosure was filed. By implementing the reagents and techniques described here, the user can obtain a product comprising nucleic acids that is considerably better for sequencing and expression analysis, achieving higher quality and a wider range of information about the sample from which the nucleic acid was isolated.

This disclosure provides data from experiments in which the technology of this invention was compared with kits that are commercially available for obtaining the same objective (Examples 4 to 8). The data show that the technology of this invention has many substantial advantages for the user, including, but not limited to, the following:
- a better yield of mRNA and other nucleic acids can be achieved from the starting sample, providing the user with more material for subsequent analysis;
- less degradation of nucleic acids isolated from the sample, enabling the user to obtain better sequence information for comparison between samples; and
- an increased number of unique RNA species in the isolated nucleic acids, thereby improving the sensitivity of the subsequent analysis.

These improvements have been observed over a wide range of different types of biological samples, demonstrating the wide applicability of this invention.

Nucleic acids can be extracted from a wax or paraffin-embedded tissue or cell sample of human or other biological origin. The sample is combined with a wax-solubilizing organic solvent to form a mixture, wherein substantially all (>95%, preferably >98%) of the wax is in the liquid phase, and at least some of the nucleic acids from the sample are dissolved. An alcohol is then added to the mixture. A precipitate or solid phase is formed before or after the adding of the alcohol that contains nucleic acids from the sample.

The organic solvent and the alcohol are then separated from the precipitate, such that at least 90%, preferably 97%, or all of the solvent or alcohol originally added to the sample is removed. The means for removal may be centrifugal separation, gravity precipitation, filtration, or column separation. The precipitate is then combined with a lysis buffer to form a lysis solution. This may be the end product, but typically the nucleic acid is isolated from the solution for further analysis. For example, beads can be added to the solution that have been adapted to bind nucleic acids. After a suitable incubation period, the beads are separated from the solution, and the nucleic acids are recovered from the beads.

The lysis buffer contains one or more non-ionic detergents and/or one or more RNase inhibiting reagents. A preferred non-ionic detergent is nonyl-phenoxypolyethoxylethanol (NP40). Other non-ionic detergent means that can be used in some instances include Triton™ X-100, Triton™ X-114, Tween™ 20 (polysorbate 20), Tween™ 40, Tween™ 60, and Tween™ 80. A preferred RNase inhibiting agent is sodium dodecyl sulfate (SDS), present in the lysis buffer at an effective concentration, for example, between 0.25% and 1% (w/v). A preferred organic solvent for the extraction is a saturated hydrocarbon comprising at least six carbon atoms, such as a linear alkane containing 10 to 20 carbon atoms or 13 to 17 carbon atoms, exemplified by hexadecane. A preferred alcohol is a saturated alcohol containing no more than five carbon atoms, exemplified by ethanol. The lysis buffer may also contain a protease, such as a serine protease, exemplified by proteinase K.

These reagents are implemented according to any effective protocol. For example, the mixture of the sample and the organic solvent can be incubated at a temperature and for a time that facilitates dissolution, such as a temperature of 55° C. for 1 to 5 minutes before adding the alcohol. Optionally, the organic solvent is removed from the precipitate before the alcohol is added. Optionally, the precipitate is dried after the alcohol wash such that less than 3% or less than 1% of the alcohol remains before the lysis buffer is added.

Where the object is to recover RNA, the nucleic acids from the sample are optionally treated with a DNase such as DNase I to remove DNA from the sample. This treatment can be done by including the DNase in the lysis buffer, adding the DNase when the buffer is contacted with the beads, during the incubation time with the beads, or after the nucleic acid is recovered from the beads. The recovered nucleic acid can be used for determining nucleic acid sequences from the sample, analyzing gene expression, or for any other purpose desired by the user.

The invention also provides a method for improving the recovery of nucleic acids in a protocol for isolating nucleic acids from wax-embedded biological samples. Standard protocols often comprises dissolving the wax-embedded sample in an organic solvent, extracting nucleic acids from the organic solvent into an aqueous buffer, and isolating the nucleic acids from the aqueous buffer. The improvement comprises one, two, three or all four of the following features in any combination: (1) using a saturated hydrocarbon comprising at least 10 carbon atoms (such as hexadecane) as the organic solvent; (2) causing the nucleic acids in the organic solvent to form a precipitate, which is then washed to remove the organic solvent and alcohol; (3) including the non-ionic detergent nonyl-phenoxypolyethoxylethanol (NP40) in the aqueous buffer; and (4) including an RNase inhibitor (such as sodium dodecyl sulfate, SDS) in the aqueous buffer.

Depending on conditions, results that can be achieved by isolating nucleic acid according to the protocol include any one, two, or more than two of the following: (1) improved yield of the nucleic acids from the sample: for example, a median yield of the nucleic acids of at least 15, 25, 35, or 50 ng/µL. (2) decreased degradation of the isolated nucleic acids: for example, a median percentage of nucleic acids or fragments in the preparation of over 200 base pairs in length (DV200) of at least 30%, 40%; 50%, or 65%. (3) an increased number of unique mRNA transcripts from isolated mRNA: for example, a median number of unique mRNA transcripts detected in isolated RNA at Cq<22 of at least 40, 60, 100, or 150; or a median number of unique genes detected in isolated DNA of at least 10,000, 12,000, or 15,000. Such qualification is determined using standard FFPE samples, such as a panel paraffin-embedded human cancer biopsy specimens collected from a variety of tissue samples, as illustrated in the Example section below.

The invention also provides various reagent combinations and kits for extracting nucleic acids from a formalin-fixed paraffin-embedded (FFPE) or other biological sample. By way of illustration, a combination or kit according to the invention may contain in separate containers: (a) an amount of a hexadecane or other saturated hydrocarbon sufficient to dissolve paraffin and at least some of the nucleic acids in the FFPE biological sample; (b) an amount of ethanol or other alcohol sufficient to remove hexadecane from the biological sample; (c) a lysis buffer formulated to dissolve nucleic acids from the sample that have been precipitated; wherein the lysis buffer contains a non-ionic detergent such as nonyl-phenoxypolyethoxylethanol (NP40), at least one protease such as proteinase K, and optionally an RNase inhibitor such as SDS. The kit optionally contains: (d) beads or other nucleic acid separation means that is adapted to bind nucleic acids from the sample that have been dissolved in the lysis buffer; and (e) a DNase.

Typically, the kit also comprises instructions for extracting nucleic acids from the FFPE biological sample. Reagents of a reagent combination may be sold separately, with the vendor providing information to consumers about how they can be combined to perform an isolation protocol according to this invention.

These and other aspects of the invention are described in more detail in the sections that follow.

BRIEF DESCRIPTION OF THE DRAWINGS

FIG. 7A especially shows that a higher number of genes was detected consistently in each of the four different FFPE samples using a kit according to this invention, with low variation in the number of genes detected per sample.

DETAILED DESCRIPTION OF THE INVENTION

Figure 1A:
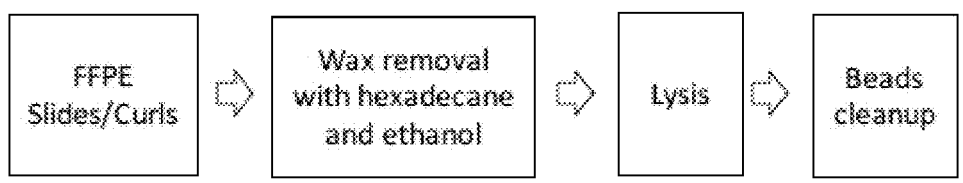
FIG. 1A is a schematic diagram showing the workflow of extracting both DNA and RNA from a FFPE biological sample.

This disclosure provides methods and kits for extracting, isolating, and/or purifying nucleic acids (such as deoxyribonucleic acids (DNA) and ribonucleic acids (RNA)) from a wax-embedded biological sample (such as a formalin-fix, paraffin-embedded (FFPE) biological sample). The methods and kits can be used to obtain extracted nucleic acids with high yield and less degradation, thus, making the nucleic acids suitable for direct subsequent analysis. The methods and kits provided are useful for subsequent nucleic acid sequencing procedures (such as sequencing) or detection by amplification (for example, by qPCR). This technology may be used to determine the DNA content and/or RNA expression profiles in the originating sample.

I. Deparaffinization of Wax-Embedded Biological Samples

Wax-embedded biological samples that can be processed according to this invention may include fractions and slices of organs, tissues, or cells isolated from a subject, such as a human or other mammal, or an immortalized cell line that is inlaid or embedded in a wax and preserved for histochemical, chemical, or biological analysis. The sample may be a tissue section (such as tissue slide or block), or a tissue section taken from a biological sample having a disease including, but not limited to, a tissue section that is taken from a biological sample determined to be cancer tissue.

Waxes that are commonly used to preserve biological samples are often composed of a mixture of long chain hydrocarbons and may include additional components, such as fatty acids, esters of fatty acids, polyethylene glycols (PEGs), and long chain alcohols. Waxes may also contain preservatives, such as dimethyl sulfoxide, to further enhance its properties. Waxes used to embed biological samples may be of natural or synthetic origin and may be derived from petroleum, coal, oil shale, animals, and/or plants. Waxes are hydrophobic and insoluble in water, but soluble in organic, nonpolar solvents. The biological sample may be embedded in a paraffin wax composed primarily of long chain hydrocarbons. Paraffin waxes may also contain mixtures of saturated linear- and iso-alkanes, naphthenes, and alkyl- and naphthene-substituted aromatic compounds. The degree of hydrocarbon chain branching and/or saturation may influence the chemical properties of the paraffin wax.

The wax-embedded biological sample may be a formalin-fixed, paraffin-embedded (FFPE) biological sample. Formalin is a water solution of formaldehyde and is often composed of 40% formaldehyde by volume (for example, about 37% formaldehyde by weight). In a FFPE biological sample, the biological sample is fixed using formaldehyde before being embedded in paraffin wax. The thickness of a wax-embedded biological sample may be between 1 and 20 μm (for example, between 1 and 18 μm, between 1 and 16 μm, between 1 and 14 μm, between 1 and 12 μm, between 1 and 10 μm, between 1 and 8 μm, between 1 and 6 μm, between 1 and 4 μm, between 1 and 2 μm, between 2 and 20 μm, between 4 and 20 μm, between 6 and 20 μm, between 8 and 20 μm, between 10 and 20 μm, between 12 and 20 μm, between 14 and 20 μm, between 16 and 20 μm, between 18 and 20 μm, between 2 and 18 μm, between 3 and 16 μm, between 4 and 14 μm, between 5 and 12 μm, between 5 and 10 μm, or between 6 and 8 μm). The methods of the invention includes the first step of removing the wax from the embedded biological sample, also referred to as deparaffinization.

The FFPE biological sample is first contacted with a wax-solubilizing agent (such as hexadecane) to form a mixture. An alcohol (such as ethanol) is then added to the mixture to help in removing the wax-solubilizing agent. Depending on conditions, the wax-solubilizing agent and the alcohol may be added to the sample simultaneously. Finally, the solubilized wax, a wax-solubilizing agent such as hexadecane, and an alcohol such as ethanol are removed from the mixture, for example, by centrifuging the mixture to form a pellet containing the desired biological sample and a supernatant containing the solubilized wax, the wax-solubilizing agent, and the alcohol. The supernatant may subsequently be removed and discarded. The mixture may be incubated at between about 50° C. and about 60° C. (for example, about 51° C., 52° C., 53° C., 54° C., 55° C., 56° C., 57° C., 58° C., or 59° C.) to further assist in dissolving and separating the wax from the sample. After the wax-solubilizing agent is added to the biological sample and the wax is dissolved, the dissolved wax and the wax-solubilizing agent may be removed from the mixture prior to the addition of the alcohol.

A wax-solubilizing agent used in the methods and kits used in this invention is typically an organic solvent, such as a saturated or unsaturated hydrocarbon. The solvent may contain linear, branched, and/or cyclic alkanes that is capable of solubilizing the wax. The wax-solubilizing agent may be a linear alkane, such as a C10-C20 linear alkane (for example, a C10, C11, C12, C13, C14, C15, C16, C17, C18, C19, or C20 linear alkane; a C11-C19, C12-C18, C13-C17, or C14-C16 linear alkane), such as hexadecane. Once the wax is solubilized, the mixture may be centrifuged and the solubilized wax and the wax-solubilizing agent may be discarded as the supernatant, the resulting pellet containing the biological sample may be washed using the alcohol to remove any residual wax-solubilizing agent. Performing an alcohol wash step may help to completely remove the wax-solubilizing agent from the biological sample, which may contribute to increasing the yield and purity of the extracted nucleic acids. After the alcohol wash step, the biological sample mixture may be centrifuged to remove the alcohol as the supernatant and collect the biological sample, now de embedded from the wax, as the pellet. The pellet may also be air-dried until any residual ethanol has evaporated.

II. Cell Lysis and Nucleic Acid Isolation

Once the biological sample is deparaffinized, the sample may be lysed using a lysis buffer to release the cellular components. A lysis buffer may be any aqueous solution that is capable of breaking open or lyse the cells in the biological sample to release the nucleic acids into the solution without degrading, fragmenting, or modifying the nucleic acids. A lysis buffer used in the methods and kits of the invention may include, for example, one or more detergents, one or more proteases, one or more salts, one or more buffering agents, and/or one or more chelating agents. A lysis buffer may also be adjusted to or kept at a desired pH range (typically, a pH of between 6 and 8; for example, a pH of 6, 6.2, 6.4, 6.6, 6.8, 7, 7.2, 7.4, 7.6, 7.8, or 8) for the most efficient lysis and to provide a stable environment for the desired cellular components.

Where only DNA is desired, the lysis buffer may further include a ribonuclease (RNase) and may not include an RNase inhibitor. Where both DNA and RNA or only RNA is desired, the lysis buffer may further include an RNase inhibitor (also referred to as an RNA enhancer) to prevent RNA degradation. Depending on the type of biological sample and the desired cellular component to be extracted, the detergents, proteases, salts, buffering agents, chelating agents, and their respective amounts and concentrations in the lysis buffer may be tailored to the specific biological sample. The components of the lysis buffer may be provided in admixture or separately added to the sample to form the lysis solution.

The deparaffinized biological sample may be contacted with a lysis buffer to form a lysis solution. The lysis solution may be incubated in a heated environment between about 50° C. and about 60° C. (for example, about 51° C., 52° C., 53° C., 54° C., 55° C., 56° C., 57° C., 58° C., or 59° C.) for 1-24 hours (for example, 2, 4, 6, 8, 10, 12, 14, 16, 18, 20, 22, or 23 hours) for efficient cellular lysis. The lysis solution may be incubated at about 55° C. for between about 1 and about 16 hours. Where RNA is to be isolated, this incubation may be about 1 hour, or at least 1 hour. Where DNA (or both DNA and RNA) is to be isolated, this incubation may be longer, such as at least 16 hours. To stop the lysis reaction (such as by inactivating the protease(s) in the lysis buffer), the lysis solution may be further incubated at between about 85° C. and about 95° C. (for example, about 90° C.) for 5-10 minutes. Subsequently, the lysis solution may be centrifuged to pellet the undesired cellular materials and isolate the nucleic acids in the supernatant for subsequent bead purification.

Detergents in the lysis buffer enable the disruption of cellular membranes and the sublization of membrane proteins and lipids. Detergents are amphipathic molecules containing both a nonpolar tail group having aliphatic or aromatic character and a polar head group. Detergents in the lysis buffer may be nonionic, anionic, cationic, zwitterionic, or a mixture thereof. Examples of detergents that may be included in a lysis buffer used in methods of the invention include, but are not limited to, NP-40, Triton X 100, Triton X-114, Tween 20 (polysorbate 20), Tween 40, Tween 60, Tween 80, 3 [(3 cholamidopropyl)dimethylammonio]-1-propanesulfonate (CHAPS), 3 [(3 cholamidopropyl)dimethylammonio]-2-hydroxy-1-propanesulfonate (CHAPSO), octyl glucoside, octyl thioglucoside, bile salts (such as cholate), and quaternary ammonium surfactants (such as cetyl trimethyl ammonium bromide (CTAB), tetradecyl trimethyl ammonium bromide (TTAB), ethyl trimethyl ammonium bromide (ETAB)). The detergent in the lysis buffer is NP-40. The amount of detergent in a lysis buffer may be optimized by one of skill in the art.

The lysis buffer may contain between 0.01% and 1% (for example, about 0.025%, about 0.05%, about 0.1%, about 0.2%, about 0.3%, about 0.4%, about 0.5%, about 0.6%, about 0.7%, about 0.8%, or about 0.9%) of a non-ionic detergent such as NP-40. The lysis buffer may contain between 0.01% and 0.5%, between 0.01% and 0.25%, or between 0.01% and 0.1% NP-40. The lysis buffer may contain between 0.05% and 1%, between 0.05% and 0.5%, between 0.05% and 0.2%, between 0.1% and 1%, or between 0.1% and 0.5% NP-40. The lysis buffer may contain about 0.05% NP 40. The lysis buffer is added to the sample to form a lysis solution. As described below, additional components for a lysis buffer may be included, either in admixture with the detergent or separately.

The lysis buffer used in the methods and kits of the invention includes one or more proteases. A protease is an enzyme that breaks down proteins into smaller peptides and amino acids by proteolysis. Proteases may be classified according to the catalytic group involved in its active site. Examples of classes of proteases include, but are not limited to, serine proteases (such as proteinase K, chymotrypsin, trypsin, elastase, plasmin, thrombin, acrosomal protease, complement C1, keratinase, collagenase, fibrinolysin, and cocoonase), cysteine proteases (such as papain, bromelain, cathepsin, calpain, caspase-1, sortase, TEV protease, and hepatitis C virus peptidase 2), threonine proteases, aspartic proteases, glutamic proteases, metalloproteases, and asparagine peptide lyases. The protease may be in admixture with other components of the lysis buffer, or may be combined with other components of the lysis buffer to form the lysis solution.

The lysis solution may further contain a buffering agent to prevent a rapid change in pH of the solution. Examples of a buffering agent include, but are not limited to, tris(hydroxymethyl)aminomethane (Tris), citric acid, acetic acid, potassium phosphate, borate, N-Cyclohexyl-2-aminoethanesulfonic acid (CHES), tris(hydroxymethyl)methylamino] propanesulfonic acid (TAPS), bicine, tricine, 3-(N-Tris-(hydroxymethyl)methylamino)-2-hydroxypropaneesulfonic acid (TAPSO), 4-(2-hydroxyethyl)-1-piperazineethanesulfonic acid (HEPES), 2-[[1,3-dihydroxy-2-(hydroxymethyl) propan-2-yl]amino]ethanesulfonic acid (TES), 3-(N-morpholino)propanesulfonic acid (MOPS), piperazine-N,N'-bis (2-ethanesulfonic acid (PIPES), cacodylate, and 2-(N-morpholino)ethanesulfonic acid (MES).

A buffering agent may maintain the pH of the lysis buffer at a pH of between 6 and 8 (for example, a pH of 6, 6.2, 6.4, 6.6, 6.8, 7, 7.2, 7.4, 7.6, 7.8, or 8) for the most efficient lysis and to provide a stable environment for the desired cellular components. The lysis buffer used in methods and kits of the invention may also contain addition reagents, such as chelating agents, reducing agents, stabilizers, organic or inorganic salts, metal ions, and/or pH indicators. A chelating agent, such as ethylenediaminetetraacetic acid (EDTA), may be included in the lysis buffer. The buffering agent may be provided in admixture with other components of the lysis buffer, or may be combined with other components of the lysis buffer to form the lysis solution.

Where both DNA and RNA or only RNA is desired from the biological sample, the lysis solution may further include an RNase inhibitor (also referred to as an RNA enhancer) to prevent RNA degradation. The RNase inhibitor may be a protein that binds to certain classes of ribonucleases. The RNase inhibitor may be a small molecule compound. The RNase inhibitor used in the lysis buffer of the methods and kits may be an aqueous solution containing SDS.

The lysis buffer may include between 0.1% SDS and 1.5% SDS (for example, between 0.1% and 1.2%, between 0.1% and 1.0%, between 0.1% and 0.8%, between 0.1% and 0.6%, between 0.1% and 0.4%, between 0.1% and 0.2%, between 0.2% and 1.5%, between 0.4% and 1.5%, between 0.6% and 1.5%, between 0.8% and 1.5%, between 1.0% and 1.5%, between 1.2% and 1.5%, or between 1.4% and 1.5% SDS). The lysis buffer used in this invention may include between 0.125% SDS and 1% SDS (for example, more than 0.125% SDS and less than or equal to 1% SDS). The lysis buffer may include between 0.1% and 1.5%, between 0.2% and 1.2%, between 0.2% and 1%, between 0.25% and 1%, between 0.2% and 0.9%, between 0.2% and 0.8%, between 0.25% and 0.7%, between 0.2% and 0.6%, between 0.25% and 0.5%, between 0.3% and 0.5%, or about 0.4% SDS. The components of the lysis buffer may be provided in admixture, or may be added separately to the sample to form the lysis solution.

The components of the lysis buffer may be provided in admixture, or may be added separately to form the lysis solution. Where only DNA is desired from the biological sample, the lysis buffer typically does not containing an RNase inhibitor. Where only DNA is desired from the biological sample, the lysis buffer may further contain an Rnase, such as RNase A, RNase H, RNase III, RNase L, and RNase P. Where only DNA is desired from the biological sample, the lysis buffer may further contain an RNase A. Moreover, if only RNA is desired, the methods may include an additional step of DNase digestion. The RNase inhibitor may be provided in admixture with other components of the lysis buffer, or may be combined with other components of the lysis buffer to form the lysis solution. In the methods and kits of this invention, one or more of the detergent, protease, buffering agent, RNase inhibitor, or any combination thereof may be provided in admixture with other components of the lysis buffer, or may be combined when forming the lysis solution. For example, the detergent, RNA inhibitor and protease may all be provided separately and one or more may be in the buffering agent.

III. Bead Purification of Isolated Nucleic Acids

The isolated nucleic acids in the supernatant as described in the previous section may be further purified using various solid-phase separation methods, such as chromatography. Many available solid-phase separation methods utilize the attractive interactions between nucleic acid molecules and silica surfaces under optional salt concentrations and pH. The solution containing the isolated nucleic acids as described in the previous section may be mixed with beads, such as magnetic beads coated with silica on their surfaces. Once the nucleic acids bind to the magnetic beads, the beads can be separated from the aqueous solution using a magnetic separator. The isolated nucleic acids can subsequently be eluted from the magnetic beads using water. The ratio of nucleic acids to magnetic beads may be optimized to improve nucleic acid yield.

Beads are adapted to bind nucleic acids by having a surface that provides binding moieties that capture DNA and/or RNA in a specific or non-specific fashion. Magnetic beads designed to isolate nucleic acids are described in Smith et al., J. Clin. Microbiol., 41:2440-2443, 2003, Miszczak et al., J. Clin. Microbiol., 49:3694-3696, 2011, and Yang et al., J. Virol. Methods, 171:195-199, 2011.

Various magnetic beads are also commercially available, such as AMPure® beads, MagJET® beads, and Magnesil Blue® beads. AMPure beads (Beckman Coulter) are magnetic particles coated with carboxyl groups (in the form of succinic acid) that can bind DNA non-specifically and reversibly. If added to the DNA in the presence of polyethylene glycol (PEG) and salt (usually NaCl), they replace the capricious gel extraction with standardized and quick, binding and elution steps. The Thermo Scientific MagJET™ mRNA Enrichment Kit is designed for purification of mRNA from total RNA samples. The oligo (dT) beads bind poly A+ RNA specifically. Typically, silica-coated beads extract total RNA, oligo (dT) beads selectively extract total mRNA, and RSV-specific beads selectively extracted RSV N gene mRNA. The choice of bead functionality is generally dependent on the target detection strategy. See Adams et al., ACS Appl Mater Interfaces. 2015 7(11):6062-9 and U.S. Pat. No. 7,527,979.

The solution containing the isolated nucleic acids may be loaded onto a column containing silica as the solid phase. The supernatant can be removed either by gravity or centrifugation (in the case of spin-columns). The isolated nucleic acids can then be eluted from the column using water. This bead purification may separate the isolated nucleic acid from an RNase inhibitor, such as SDS.

IV. DNase Digestion

As described above, if RNA is the desired material, the protocol may include an additional step of DNase digestion once the nucleic acids are isolated. A DNase (such as DNase I or DNase II) may be used to catalyze the hydrolytic cleavage of phosphodiester linkages in the DNA backbone, thus degrading DNA. An exemplary DNase used in this invention is DNase I. For example, DNase I and its compatible buffer may be added to a solution containing isolated DNA and RNA. The resulting mixture may be incubated at 37° C., for 5-10 minutes for the enzymatic DNA degradation by DNase I to take place. To stop the reaction, a chelating agent (such as EDTA) may be added to the solution and the solution may be incubated at 70-80° C. for 5-10 minutes. An additional bead purification may be performed to isolate the RNA molecules, which have greater affinity to the silica surfaces relative to the degraded DNA fragments.

Embodiments of the Invention

This section outlines features of certain embodiments of the invention, without limitation. Other features and embodiments are provided elsewhere in this disclosure.

The invention includes methods and kits for extracting nucleic acids (such as deoxyribonucleic acids (DNA) or ribonucleic acids (RNA)) from a wax-embedded biological sample (such as a formalin-fixed, paraffin-embedded (FFPE) biological sample). The methods and kits of this invention may use an alkane, such as hexadecane, to solubilize the wax (such as paraffin). Hexadecane dissolves paraffin easily, is much less toxic than xylene, and can be removed cleanly by one or more ethanol washes, which improves the yield of nucleic acid extraction.

The lysis buffer used in the methods of this invention may contain an RNase inhibitor if the desired nucleic acid is RNA only or both DNA and RNA. The lysis buffer may also contain a detergent (such as NP-40) and a protease (such as proteinase K). The methods and kits provide extracted nucleic acids with high yield and less degradation, thus, making the nucleic acids suitable for subsequent analysis including, but not limited to, nucleic acid sequencing and gene expression analysis (such as by PCR). In certain embodiments, the nucleic acids extracted using the methods and kits are suitable for direct subsequent analysis: for example, genomic sequencing, without the need for pre-amplification.

In one aspect, the invention provides a method of extracting nucleic acids from a wax-embedded biological sample by (a) contacting the biological sample with a wax-solubilizing agent to form a mixture; (b) adding an alcohol to the mixture; (c) removing the wax solubilized in the wax-solubilizing agent and the alcohol from the mixture; (d) contacting the biological sample with a lysis buffer comprising NP-40 to form a lysis solution; and (e) isolating the nucleic acids from the lysis solution using beads.

In another aspect, the invention provides a method of extracting nucleic acids from a wax-embedded biological sample by (a) contacting the biological sample with a wax-solubilizing agent to form a mixture; (b) adding an alcohol to the mixture; (c) removing the wax solubilized in the wax-solubilizing agent and the alcohol from the mixture; (d) contacting the biological sample with a lysis buffer comprising between 0.25% and 1% of sodium dodecyl sulfate (SDS) to form a lysis solution; and (e) isolating the nucleic acids from the lysis solution using beads.

In another aspect, the invention provides a method of extracting nucleic acids from a wax-embedded biological sample by (a) contacting the biological sample with a wax-solubilizing agent to form a mixture; (b) adding an alcohol to the mixture; (c) removing the wax solubilized in the wax-solubilizing agent and the alcohol from the mixture; (d) contacting the biological sample with a lysis buffer comprising NP-40 and sodium dodecyl sulfate (SDS) to form a lysis solution; and (e) isolating the nucleic acids from the lysis solution using beads.

In some embodiments of the previous three aspects of the invention, the mixture from step (a) is incubated at about 55° C. for 1 to 5 minutes prior to step (b). In some embodiments, the wax-solubilizing agent is removed after step (a) and prior to step (b). In some embodiments, the wax-solubilizing agent and the alcohol are added simultaneously to the wax-embedded biological sample. In some embodiments, after step (c), the biological sample is dried prior to step (d).

In some embodiments of the previous three aspects of the invention, when the nucleic acids are ribonucleic acids (RNA), the method further comprises: step (f) removing deoxyribonucleic acids (DNA) by contacting the nucleic acids isolated in step (e) with a DNase. In particular embodiments, the DNase is DNase I. In some embodiments, the method further comprises: step (g) isolating the RNA using magnetic beads.

In some embodiments of the previous three aspects of the invention, the lysis buffer comprises a protease. In particular embodiments, the protease is selected from the group consisting of a serine protease, a cysteine protease, a threonine protease, an aspartic protease, a glutamic protease, a metalloprotease, and an asparagine peptide lyase. In particular embodiments, the protease is a serine protease (such as proteinase K).

In some embodiments of the previous three aspects of the invention, the lysis buffer comprises at least one detergent. In particular embodiments, the detergent is selected from the group consisting of NP 40, Triton X-100, Triton X-114, Tween 20 (polysorbate 20), Tween 40, Tween 60, and Tween 80. In some embodiments, the lysis buffer comprises an RNase inhibitor (such as sodium dodecyl sulfate (SDS)). In some embodiments, the lysis buffer comprises an RNase.

In another aspect, the invention provides a method of extracting deoxyribonucleic acids (DNA) from a wax-embedded biological sample by (a) contacting the biological sample with a wax-solubilizing agent to form a mixture; (b) adding an alcohol to the mixture; (c) removing the wax solubilized in the wax-solubilizing agent and the alcohol from the mixture; (d) contacting the biological sample with a lysis buffer to form a lysis solution; and (e) isolating the nucleic acids from the lysis solution using beads, wherein the lysis buffer does not contain any SDS.

In some embodiments of any of the previous aspects of the invention, the beads used in the methods are magnetic beads. In some embodiments, the wax-solubilizing agent is a linear alkane, such as a C10-C20 linear alkane (such as a C13-C17 linear alkane). In particular embodiments, the linear alkane is hexadecane.

In some embodiments of any of the previous aspects of the invention, the wax-embedded biological sample is a paraffin-embedded biological sample (such as a formalin-fixed, paraffin-embedded (FFPE) biological sample). In some embodiments, the biological sample is a human tissue sample.

In another aspect, the invention also features a method of extracting nucleic acids from a formalin-fixed, paraffin-embedded (FFPE) biological sample by: (a) contacting the FFPE biological sample with hexadecane to form a mixture, wherein the paraffin in the FFPE biological sample is solubilized in the hexadecane; (b) centrifuging the mixture to form a supernatant containing the hexadecane and the solubilized paraffin and a pellet containing the biological sample; (c) removing and discarding the supernatant; (d) adding ethanol to the pellet; (e) removing the ethanol from the pellet; (f) drying the pellet; (g) contacting the pellet with a lysis buffer to form a lysis solution; and (h) isolating the nucleic acids from the lysis solution using beads, wherein the lysis buffer comprises NP-40, sodium dodecyl sulfate (SDS), and proteinase K.

In some embodiments of this aspect, when the nucleic acids are ribonucleic acids (RNA), the method further comprises: step (i) removing deoxyribonucleic acids (DNA) by contacting the nucleic acids isolated in step (h) with a DNase (such as DNase I). In particular embodiments, the method further comprises: step (j) isolating the RNA using beads (such as magnetic beads).

In yet another aspect, the invention also features a kit for extracting nucleic acids from a formalin-fixed, paraffin-embedded (FFPE) biological sample. The kit includes: (a) instructions for extracting nucleic acids from the FFPE biological sample; (b) hexadecane; (c) ethanol; (d) a lysis buffer comprising proteinase K and NP-40; and (e) beads. In some embodiments, the lysis buffer in the kit includes an RNase inhibitor (such as sodium dodecyl sulfate (SDS)). In some embodiments, the lysis buffer in the kit further includes (f) a DNase (such as DNase I).

Definitions

In the context of this disclosure, the term "wax-embedded biological sample" refers to one or more fractions or slices of organs, tissues (such as cancer tissue sections, blocks, or slides), or cells isolated from a subject (such as a human) or an immortalized cell line that are inlaid or embedded in a wax and preserved for subsequent histochemical, chemical, or biological analysis. Paraffin is an example of a wax that may be used for such purpose. The wax may also contain preservatives to enhance its properties and the stability of the biological sample. The biological sample may be fixed using formaldehyde before being embedded in the wax.

The term "wax-solubilizing agent" refers to an organic solvent used to solubilize and remove the wax (such as paraffin) from the wax-embedded biological sample. A wax-solubilizing agent may be a solvent containing linear, branched, and/or cyclic alkanes that is capable of solubilizing the wax. The wax-solubilizing agent may be a linear alkane, such as a C10-C20 linear alkane (for example, a C10, C11, C12, C13, C14, C15, C16, C17, C18, C19, or C20 linear alkane; a C11-C19, C12-C18, C13-C17, or C14-C16 linear alkane) such as hexadecane.

The term "deparaffinize" or "deparaffinization" refers to the process of removing paraffin from a FFPE biological sample, for example, by solubilizing the paraffin in a wax-solubilizing agent, such as hexadecane.

The term "lysis buffer" refers to an aqueous buffer solution used to break open or lyse the cells in a biological sample to release the nucleic acids into the solution without degrading, fragmenting, or modifying the nucleic acids. A lysis buffer often contains a detergent and a protease. If both DNA and RNA or only RNA is desired as the extracted nucleic acids, the lysis buffer may further contain an RNase inhibitor (such as a solution containing sodium dodecyl sulfate (SDS)), which functions to prevent RNA degradation.

A lysis buffer may also include buffering agents, chelating agents, or other salts. The lysis buffer used in the invention may include between 0.1% SDS and 1.5% SDS (for example, between 0.1% and 1.2%, between 0.1% and 1.0%, between 0.1% and 0.8%, between 0.1% and 0.6%, between 0.1% and 0.4%, between 0.1% and 0.2%, between 0.2% and 1.5%, between 0.4% and 1.5%, between 0.6% and 1.5%, between 0.8% and 1.5%, between 1.0% and 1.5%, between 1.2% and 1.5%, or between 1.4% and 1.5% SDS). The lysis buffer may include between 0.125% SDS and 1% SDS (for example, more than 0.125% SDS and less than or equal to 1% SDS). The lysis buffer may include between 0.1% and 1.5%, between 0.2% and 1.2%, between 0.2% and 1%, between 0.25% and 1%, between 0.2% and 0.9%, between 0.2% and 0.8%, between 0.25% and 0.7%, between 0.2% and 0.6%, between 0.25% and 0.5%, between 0.3% and 0.5%, or about 0.4% SDS. The components of the lysis buffer may be provided in admixture, or may be added separately to the sample to form the lysis solution.

The term "detergent" refers to a chemical agent in the lysis buffer that disrupts cellular membranes and solubilizes membrane proteins and lipids during cell lysis. Detergents are amphipathic molecules containing both a nonpolar tail group having aliphatic or aromatic character and a polar head group. Detergents in the lysis buffer may be nonionic, anionic, cationic, zwitterionic, or a mixture thereof.

The term "RNase inhibitor" or "RNA enhancer" refers to a small molecule compound used to inhibit RNA degradation by RNase. An RNase inhibitor or RNA enhancer is a component of the lysis buffer when both DNA and RNA or only RNA is desired. An RNase inhibitor or RNA enhancer may be a solution containing SDS. When both DNA and RNA or only RNA is desired, the lysis buffer may include more than 0.125% SDS and less than or equal to 1% SDS. The lysis buffer may include between 0.1% and 1.5%, between 0.2% and 1.2%, between 0.25% and 1%, between 0.2% and 0.8%, between 0.2% and 0.6%, between 0.25% and 0.7%, between 0.25% and 0.5%, between 0.3% and 0.5%, or about 0.4% SDS.

The term "between" refers to any quantity within the range indicated and enclosing each of the ends of the range indicated. For example, between 0.25% and 0.5% of SDS refers to any quantity within 0.25% and 0.5%, as well as 0.25% and 0.5% SDS.

The term "about" refers to a range of values that is ±10% of a specific value. For example, "about 55° C." includes ±10% of 55° C., or from 49.5° C. to 60.5° C. Such a range performs the desired function or achieves the desired result. For example, "about" may refer to an amount that is within less than 10% of, within less than 5% of, within less than 1% of, within less than 0.1% of, and within less than 0.01% of the stated value.

Other inventive products, methods, and features that can be used alone or in combination with the aforesaid technology are evidenced by the description and examples that follow.

EXAMPLES

The invention will be described in greater detail by way of specific examples. The following examples are offered for illustrative purposes, and are not intended to limit practice of the invention in any manner. Those of skill in the art will readily recognize a variety of noncritical parameters that can be changed or modified to yield essentially the same results.

Example 1A: Protocol for Extracting (1) DNA and RNA and (2) Only DNA from FFPE Biological Samples (FIG. 1A)

Extract DNA/RNA
1. Add FFPE samples to a 1.5 mL tube:
   If using FFPE slides: Carefully transfer the FFPE samples from the glass slides into a 1.5 mL tube with a scalpel or blade.
   If using FFPE curls: Transfer one to four FFPE sections to one 1.5 mL tube.
2. Add 1 mL of hexadecane to each 1.5 mL tube containing the FFPE samples and vortex at the maximum speed for 10 seconds.
   If the tube still contains undissolved paraffin, incubate at 55° C. for 3 min to completely melt the paraffin.
3. Centrifuge at 15,000×g for 2 minutes at room temperature.
4. Remove the supernatant by pipetting. Do not remove any of the pellet.
5. Add 1 mL of 100% ethanol to each tube and mix by vortexing at the maximum speed for 10 seconds. Centrifuge at 15,000×g for 2 minutes at room temperature.

6. Remove the supernatant by pipetting. Do not remove any of the pellet.
7. Air dry the pellet for 10 minutes at room temperature.
8. Isolate DNA and RNA:

| Component in the Lysis Buffer | Volume if RNA is desired (isolating both DNA and RNA) (µL) | Volume if RNA is NOT desired (isolating DNA only) (µL) |
| --- | --- | --- |
| Tris-buffered saline containing NP-40; Tris-EDTA buffer | 100 | 100 |
| RNase inhibitor (also referred to as RNA enhancer): solution containing SDS | 4 | — |
| Proteinase K | 4 | 4 |
| Total | 108 | 104 |

9. Mix by vortexing at medium speed for a few seconds. Then centrifuge the tubes briefly.
10. Incubate the tubes at 55° C. overnight (about 16 hours).
11. Incubate the tubes at 90° C. for 10 minutes.
12. Centrifuge at 15,000×g for 2 minutes at room temperature. Transfer 100 µL of the supernatant to a new tube for bead clean up. Discard the pellet.

Perform Bead Cleanup
1. Resuspend the magnetic beads by vortexing the bottle of beads at maximum speed for 20 seconds.
2. In the existing 1.5 mL tube, add the beads and a purification buffer containing 20% PEG and 2.5 M NaCl to the supernatant from step 11 above using volumes shown:

| Component | Volume (µL) |
| --- | --- |
| Supernatant | 100 |
| Magnetic beads | 100 |
| Purification buffer | 40 |
| Total | 240 |

3. Mix well by pipetting up and down and then vortexing at maximum speed for 15 seconds. Centrifuge the tubes briefly.
4. Incubate at room temperature for 10 minutes.
5. Place the tubes on a magnetic separator for 2 minutes.
6. With the tubes still on the separator, remove and discard the supernatant by pipetting.
7. With the tubes still on the separator, add 400 µL of 80% ethanol to each tube to wash the beads, and incubate for 1 minute. Remove and discard ethanol.
8. Repeat step 7 twice with 400 µL of 80% ethanol.
9. Remove any remaining ethanol, and then place the tubes in a rack. Dry the beads at 37° C. for 1 minute (or air dry for 10 minutes).
10. Add 15 µL of Tris-EDTA to each tube. Mix well by pipetting up and down and vortexing. Centrifuge the tubes briefly.
11. Incubate the tubes at room temperature for 2 minutes.
12. Place the tubes on a magnetic separator for 2 minutes.
13. Transfer the eluate to a new 1.5 mL tube.

Figure 1B:
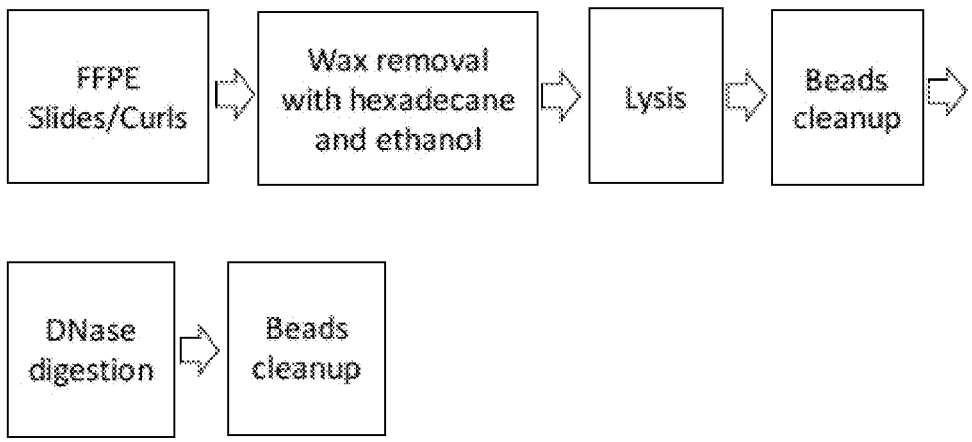
FIG. 1B is a schematic diagram showing the workflow of extracting only RNA from a FFPE biological sample.

Example 1B: Protocol for Extracting Only RNA from FFPE Biological Samples (FIG. 1B) Extract RNA 1. Add FFPE samples to a 1.5 mL tube:
If using FFPE slides: Carefully transfer the FFPE samples from the glass slides into a 1.5 mL tube with a scalpel or blade.
If using FFPE curls: Transfer 1-4 FFPE sections to one 1.5 mL tube.
2. Add 1 mL of hexadecane to each 1.5 mL tube containing the FFPE samples and vortex at the maximum speed for 10 seconds.
If the tube still contains undissolved paraffin, incubate at 55° C. for 3 minutes to completely melt the paraffin.
3. Centrifuge at 15,000×g for 2 minutes at room temperature.
4. Remove the supernatant by pipetting. Do not remove any of the pellet.
5. Add 1 mL of 100% ethanol to each tube and mix by vortexing at the maximum speed for 10 seconds. Centrifuge at 15,000×g for 2 minutes at room temperature.
6. Remove the supernatant by pipetting. Do not remove any of the pellet.
7. Air-dry the pellet at room temperature for 10 minutes or until all residual ethanol has evaporated.
8. Isolate nucleic acids:

| Component in the Lysis Buffer | Volume (µL) |
| --- | --- |
| Tris-buffered saline containing NP-40; Tris-EDTA buffer | 100 |
| RNase inhibitor (also referred to as RNA enhancer): solution containing SDS | 4 |
| Proteinase K | 4 |
| Total | 108 |

Mix by vortexing at medium speed for a few seconds. Centrifuge the tubes briefly at low speed.
9. Incubate the tubes at 55° C. for 1 hour.
10. Incubate the tubes at 90° C. for 10 minutes.
11. Centrifuge at 15,000×g for 2 minutes at room temperature. Transfer 100 µL of the supernatant to a new tube for bead cleanup. Discard the pellet.
Perform Bead Cleanup
1. Resuspend the magnetic beads by vortexing the bottle of beads at maximum speed for 20 seconds.
2. In the existing 1.5 mL tube, add the beads and a purification buffer containing 20% PEG and 2.5 M NaCl to the supernatant from step 11 above using volumes shown:

| Component | Volume (µL) |
| --- | --- |
| Supernatant | 100 |
| Magnetic beads | 78 |
| Purification buffer | 62 |
| Total | 240 |

3. Mix well by pipetting up and down and then vortexing at maximum speed for 10 seconds. Centrifuge the tubes briefly at low speed.
4. Incubate at room temperature for 10 minutes.
5. Place the tubes on a magnetic separator for 2 minutes.
6. Without disturbing the beads, and keeping the tubes on the magnetic separator, use a pipette to remove and discard the supernatant.
7. Wash the beads with 80% ethanol:
   a. Keeping the tubes on the separator, add 400 µL of 80% ethanol to each tube to wash the beads.
   b. Incubate the tubes at room temperature for 1 minute.
   c. Without disturbing the beads, and keeping the tubes on the magnetic separator, remove and discard the ethanol.
   d. Repeat steps a-c twice.
8. Remove any remaining ethanol. Transfer the tubes to a rack and dry the beads at 37° C. for 1 minute (or air-dry at room temperature for 10 minutes).
9. Prepare the eluate:
   a. Add 17 µL of Tris-EDTA to each tube. Mix well by pipetting up and down and vortexing. Centrifuge the tubes briefly at low speed.
   b. Incubate the tubes at room temperature for 2 minutes.
   c. Place the tubes on a magnetic separator for 2 minutes.
10. Without disturbing the beads, and keeping the tubes on the magnetic separator, transfer the eluate to a new 1.5 mL tube for DNase I digestion.
Perform DNase I Digestion
1. Add 2 µL of 10× DNase reaction buffer and 1 µL DNase I to the eluate.
2. Incubate the tubes at 37° C. for 10 minutes.
3. Add 2 µL 50 mM EDTA to each tube. Vortex, centrifuge briefly, and incubate at 75° C. for 10 minutes.
4. Transfer the tubes to a rack and allow them to cool to room temperature.
5. Add 22 µL of the magnetic beads and 9 µL of a purification buffer containing 20% PEG and 2.5 M NaCl.
6. Mix well by pipetting up and down and then vortexing at maximum speed for 10 seconds. Centrifuge the tubes at low speed briefly.
7. Incubate at room temperature for 10 minutes.
8. Place the tubes on a magnetic separator for 2 minutes.
9. Without disturbing the beads, and keeping the tubes on the magnetic separator, use a pipette to remove and discard the supernatant.
10. Wash the beads with 80% ethanol:
    a. Keeping the tubes on the separator, add 100 µL of 80% ethanol to each tube to wash the beads.
    b. Incubate the tubes at room temperature for 1 minute.
    c. Without disturbing the beads, and keeping the tubes on the magnetic separator, remove and discard the ethanol.
    d. Repeat steps a-c twice.
11. Remove any remaining ethanol. Transfer the tubes to a rack and dry the beads at 37° C. for 1 minute (or air-dry at room temperature for 10 minutes).
    a. Add 20 µL of Tris-EDTA to each tube. Mix well by pipetting up and down and vortexing. Centrifuge the tubes at low speed briefly.
    b. Incubate the tubes at room temperature for 2 minutes.
    c. Place the tubes on a magnetic separator for 2 minutes.
12. Without disturbing the beads, and keeping the tubes on the magnetic separator, transfer the eluate to a new 1.5 mL tube.
13. The RNA samples can be quantified and qualified immediately after extraction or stored at −80° C. for long term storage.

Example 2: Effect of NP-40 and SDS Concentration on DNA Yield

Figure 2:
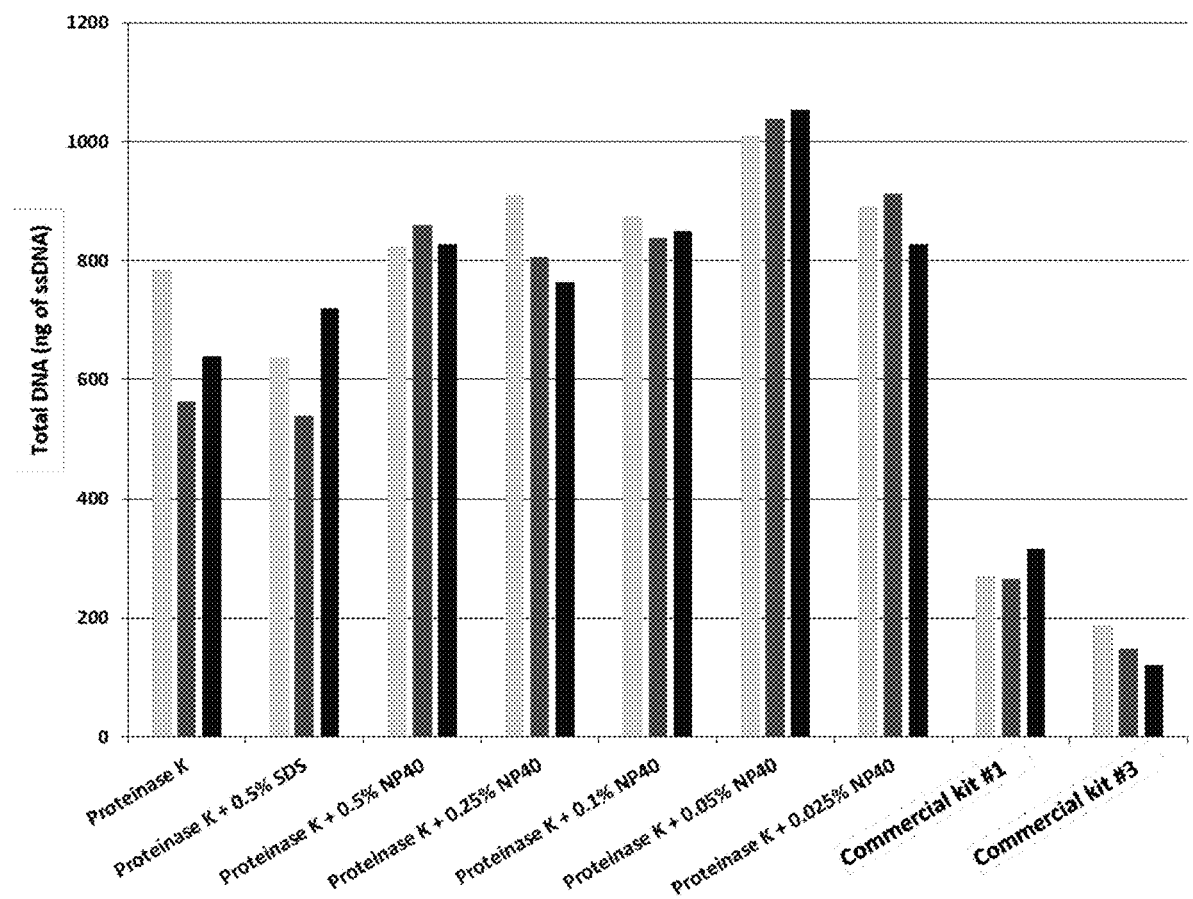
FIG. 2 is a bar graph comparing the amounts of DNA obtained using various lysis buffers containing NP-40 or SDS, as well as the amounts of DNA obtained using two commercial kits.

Nucleic acids were extracted from an FFPE sample using a lysis buffer containing proteinase K alone, or in combination with either SDS or NP-40. Other aspects of the nucleic acid extraction were similar to the workflow described in Examples 1A and 1B. The total DNA number was quantified by qPCR (in triplicate), and back-calculated to obtain the total amount of dsDNA in nanograms (FIG. 2).

A superior yield of DNA was obtained (a 2-fold increase) compared with the DNA yield obtained with commercial kits and methods (the commercial kits #1 and #3 were also used in subsequent comparisons described in the examples below). The addition of NP-40 to the proteinase K lysis buffer was shown to enhance DNA yield, with a concentration 0.05% NP-40 resulting in the highest DNA yield.

Example 3: Effect of SDS Concentration on RNA Yield

Figures 3A, 3B:
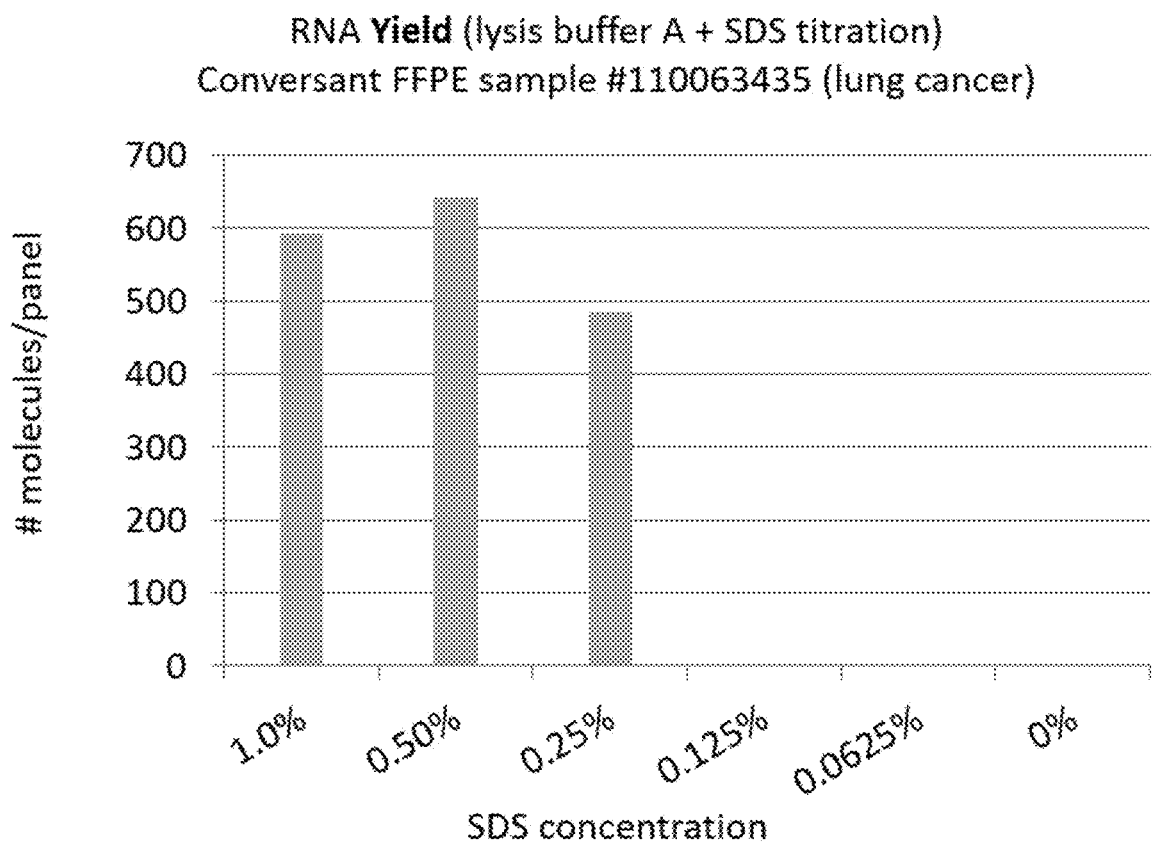
FIG. 3A is a bar graph comparing the amounts of RNA obtained using various lysis buffers containing different amounts of SDS.
FIG. 3B is a table showing that percent of SDS used in the lysis buffer was not found to adversely affect either the amount of RNA extracted using beads or downstream analysis by qPCR.

FFPE samples from lung cancer tissue sections were prepared using methods similar to those described in Examples 1A and 1B. SDS was added at different concentrations to a lysis buffer containing proteinase K and 0.05% NP-40. An SDS concentration between 0.25% and 1% was found to maximize RNA yield, as measured by digital PCR of cDNA obtained from the RNA (FIG. 3A). As the amount of NP 40 in the lysis buffer was previously shown to enable complete lysis (including lysis of the nucleus) to obtain high DNA yield, as shown in Example 2, the SDS-based improvement in RNA yield is attributable to its function as an RNase inhibitor. The percent of SDS used in the lysis buffer was not found to adversely affect either the amount of RNA extracted using beads or downstream analysis by qPCR (FIG. 3B). Accordingly, SDS can be present during the bead cleanup step without adverse effect.

Examples 4-7 assess the quality of RNA obtained using a kit according to the invention in methods similar to those described in Examples 1A and 1B, compared with RNA obtained using three commercial kits (following the methods prescribed by the commercial kits). Commercial Kit #1 is QIAGEN's AllPrep™ kit, Commercial Kit #2 is QIAGEN's miRNeasy™ kit, and Commercial Kit #3 is Thermo Fisher's Recoverall™ Kit.

Example 4: Comparison of RNA Quality Using Different Kits

Figure 4:
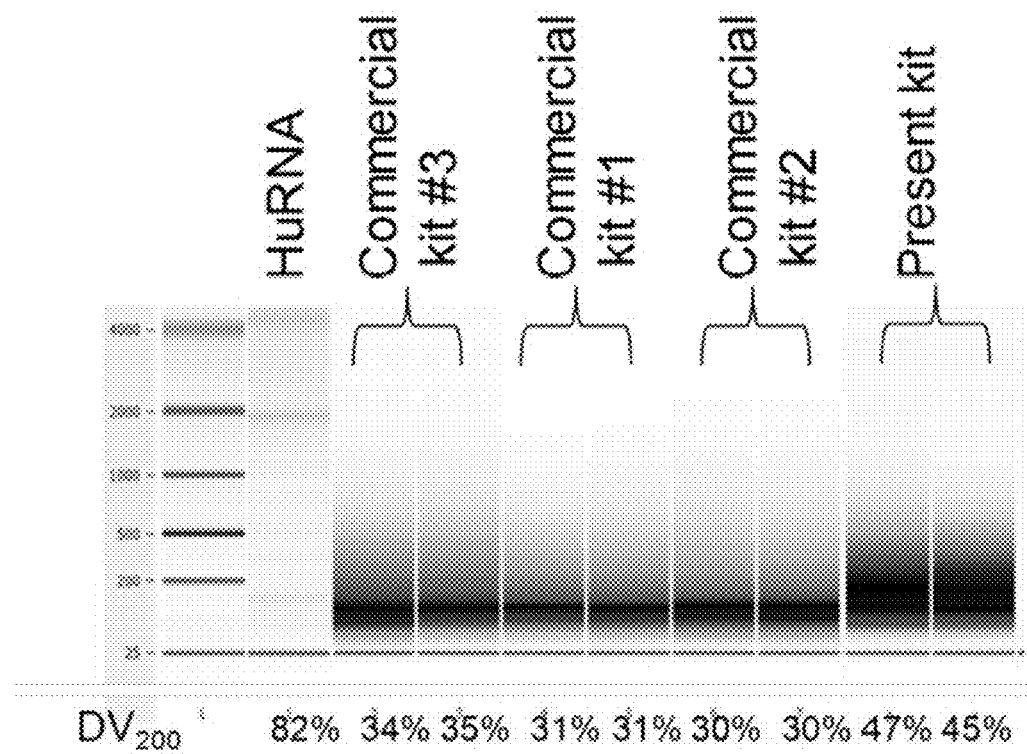
FIG. 4 is a Northern blot comparing the quality of RNA extracted using a kit according to the invention and the qualities of RNA extracted using various commercial extraction kits. All RNAs were extracted from FFPE lung cancer curls from the same block.

RNA was obtained from FFPE lung cancer curls from the same block, using the workflow described in Example 1B and the workflows of the three commercial kits. A Northern blot was performed to compare the quality of RNA extracted using a kit according to the invention compared with the three commercial extraction kits (FIG. 4). The RNA extracted using the kit had a higher average fragment length, indicating less fragmentation, than RNA extracted using the three commercially available kits. Specifically, the DV200 value (which is the percentage of RNA above 200 nucleotides) was about 45% or higher, which was at least 10% higher than the commercially available kits.

Example 5: Comparison of Target Detection by qPCR Using Different Kits

Figures 5A, 5B:
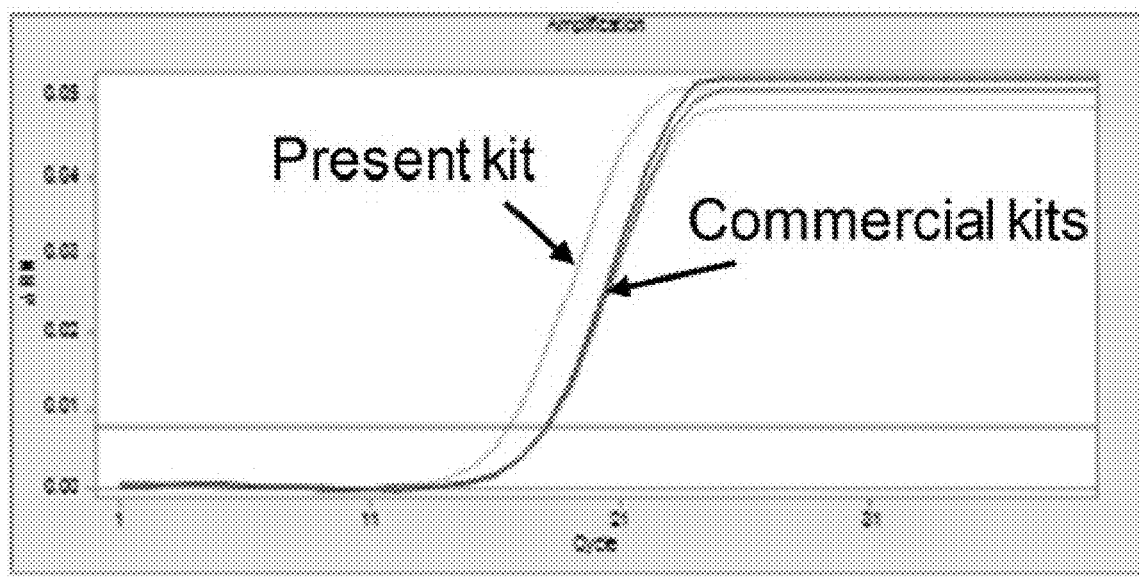
FIG. 5A is a quantitative PCR (qPCR) curve comparing the amount of CX3CL1 cDNA obtained by reverse transcription of RNA extracted using different kits.
FIG. 5B is a table showing gene expressions detected using RNA extracted using different kits.

RNA was obtained as described in Example 4, and 1 µl of extracted RNA was used for reverse transcription to make cDNA. Targets were detected by quantitative PCR (qPCR). FIG. 5A is a qPCR curve showing a lower Ct for detection of a specific target when using RNA extracted with a kit according to the invention compared with the three commercial kits. FIG. 5B is a table showing an increase in the number of targets detected (total assays detected) by qPCR using the kit compared with the three commercial kits. The kit enabled a higher percentage of targets to be detected (a 20% relative increase, or at least a 10% absolute increase) at a given quantification cycle (for example, a Cq of more than 20, such as 22), compared with the three commercial kits.

Example 6: Comparison of RNA Libraries Generated from RNA Extracted Using Different Kits RNA sequencing libraries (cDNA sequences adapted for sequencing) were generated by the TruSeq RNA Access™ Kit, using 50 ng of RNA extracted with a kit according to the invention and each of three commercial extraction kits (QIAGEN's miRNeasy and AllPrep kits, and Thermo Fisher's RecoverAll™ kit).

Figure 6:
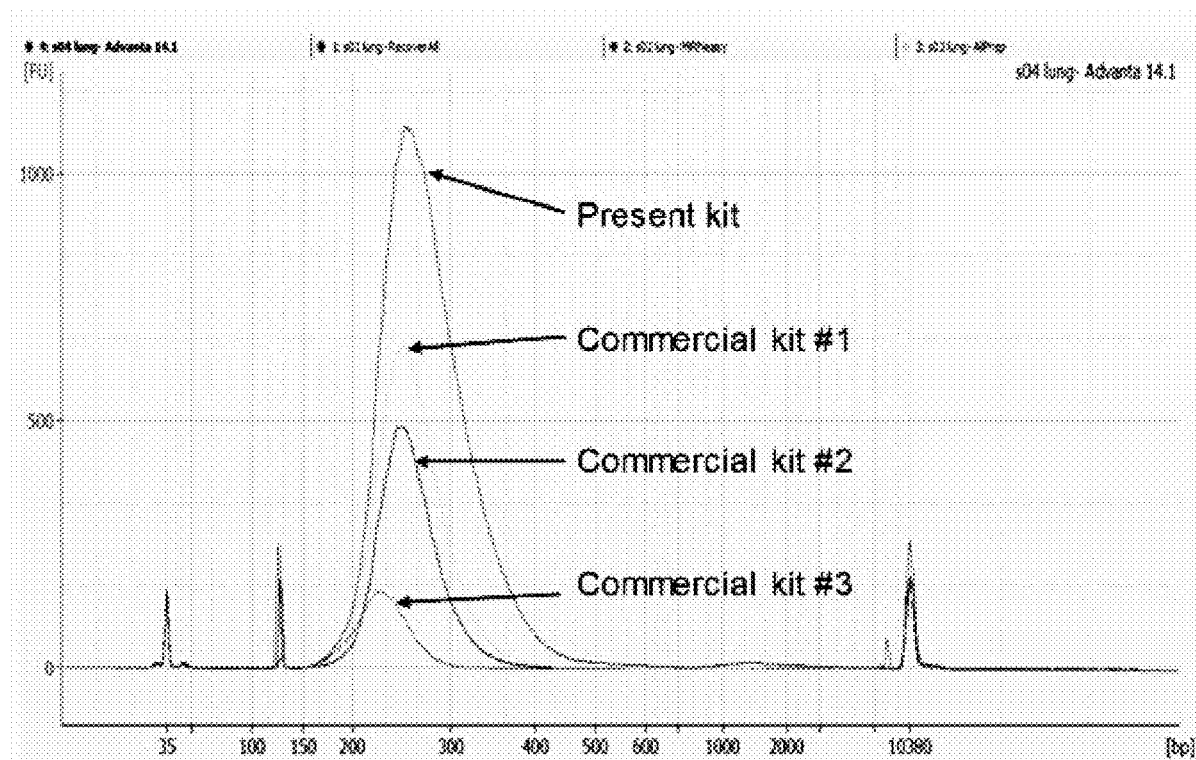
FIG. 6 is an electropherogram comparing the library yield and size distribution of RNA extracted using various commercial extraction kits.

As shown in FIG. 6, an electropherogram obtained using an Agilent 2100 Bioanalyzer™ compares the library yield and size distribution. RNA extracted using the present kit resulted in a higher library yield given the same RNA input, indicating the present kit enables extraction of higher quality (less fragmented) RNA than that of RNA extracted using the commercially available kits. Thus, the present kit provided extracted RNA that is of higher quality and more suitable for RNA sequencing compared with RNA extracted using the commercially available kits. The present kit enabled a higher yield in the RNA sequencing library compared with the commercially available kits (for example, at least a 50% relative increase given the same amount of input RNA).

Figure 7A:
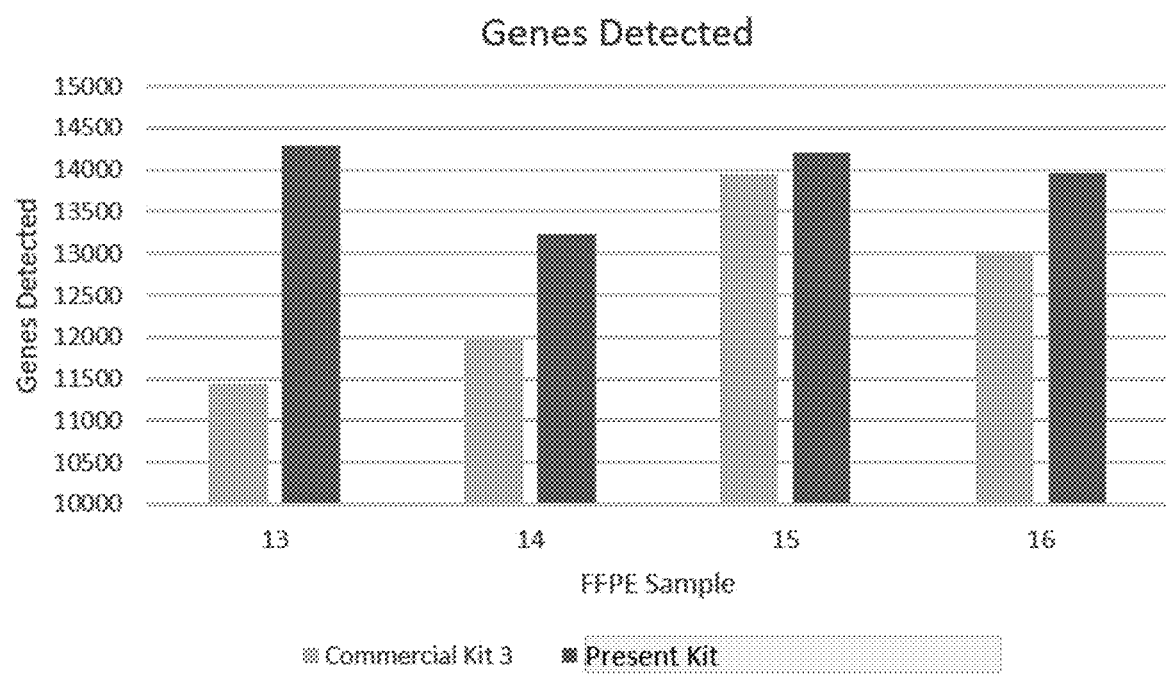
FIG. 7A and FIG. 7B are bar graphs showing the RNA extracted using a kit according to the invention (compared with commercial kits) enabled a higher number of genes to be detected by RNA sequencing.

Example 7: Comparison of RNA Libraries Generated from RNA Extracted Using Different Kits RNA sequencing libraries were obtained from RNA extracted with a kit according to the invention and commercial kits. As shown in FIG. 7A, RNA extracted using the present kit (compared with a commercial kit) enabled a higher number of genes to be detected by RNA sequencing, across four samples, with low variation in the number of genes detected per sample.

Figure 7B:
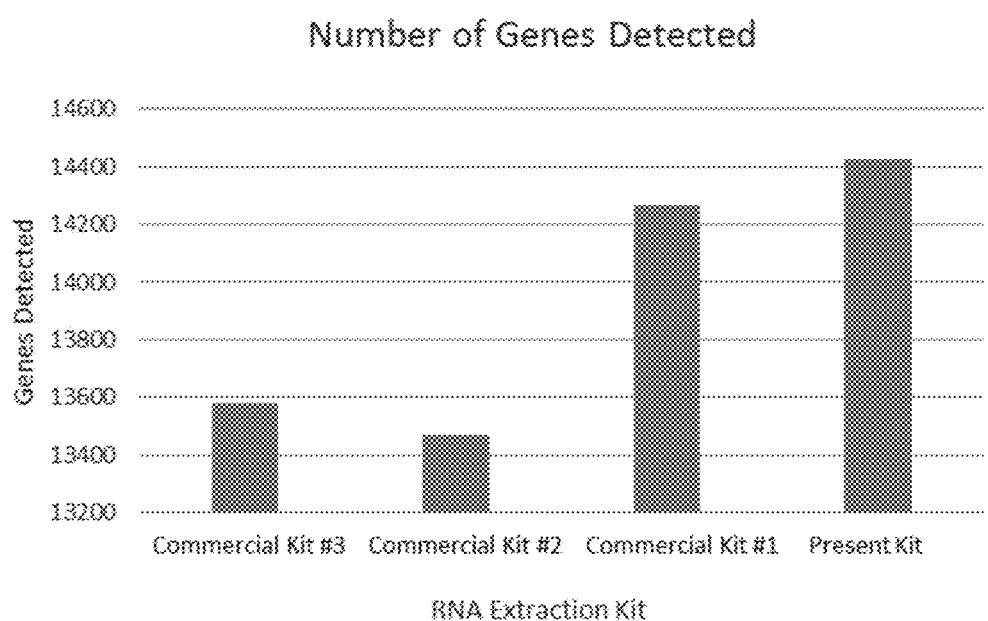

As shown in FIG. 7B, RNA extracted using the present kit (compared with the three commercial kits) enabled a higher number of genes to be detected by RNA sequencing (at least 100 more genes were detected).

The present kit enabled half the standard deviation in number of genes detected across samples or less, compared with a commercial kit. Further, at least 100 more genes were detected using RNA obtained from the present kit compared with the three commercial kits.

Example 8: Quality Control for Better Recovery of Nucleic Acids

The technology provided in this disclosure was developed for use as a kit of reagents for commercial distribution. In the following example, nucleic acids were extracted from multiple paraffin (FFPE) embedded samples using both the present kit and a commercially available kit from Qiagen (Qiagen™ miRNeasy kit). Total RNA yield and RNA quality was determined for the nucleic acids extracted by each kit from the various samples.

Additionally, the number of distinct RNA species identified from the extracted nucleic acids was evaluated using the Advanta™ TO Gene Expression Assay Panel (Fluidigm Corp., South San Francisco, Calif.). This panel includes PCR assays for a panel of 91 immuno-oncology genes and 5 reference genes and enables cellular profiling and biomarker identification using qPCR. The paraffin embedded samples used in this example were from the following sources:

| Tissue of origin | Number of samples |
| --- | --- |
| Colonic | 4 |
| Endometrial structure | 1 |
| Fallopian structure | 2 |
| Kidney structure | 12 |
| Liver structure | 2 |
| Lung structure | 2 |
| Malignant tumor of unknown origin | 3 |
| Ovarian structure | 7 |
| Stomach structure | 2 |
| Total | 35 |

The quality criteria for the kit were as follows:
1) For total yield of standard samples (HD783 reference material, Horizon Discovery, United Kingdom): Measure overall RNA concentration by nanodrop analysis. Objective: ≥5 ng/µL.
2) For DV200 (the percentage of RNA fragments recovered that are 200 or more nucleotides in length): Measure RNA fragment size by RNA sequencing QC. Objective: high as possible
3) For number of RNA species: Determine the target RNAs detected by the Fluidigm Advanta™ Immuno-Oncology Gene Expression Assay Panels at a Cq value below 22 (stringent) or 28 (permissive).

Figures 8A, 8B:
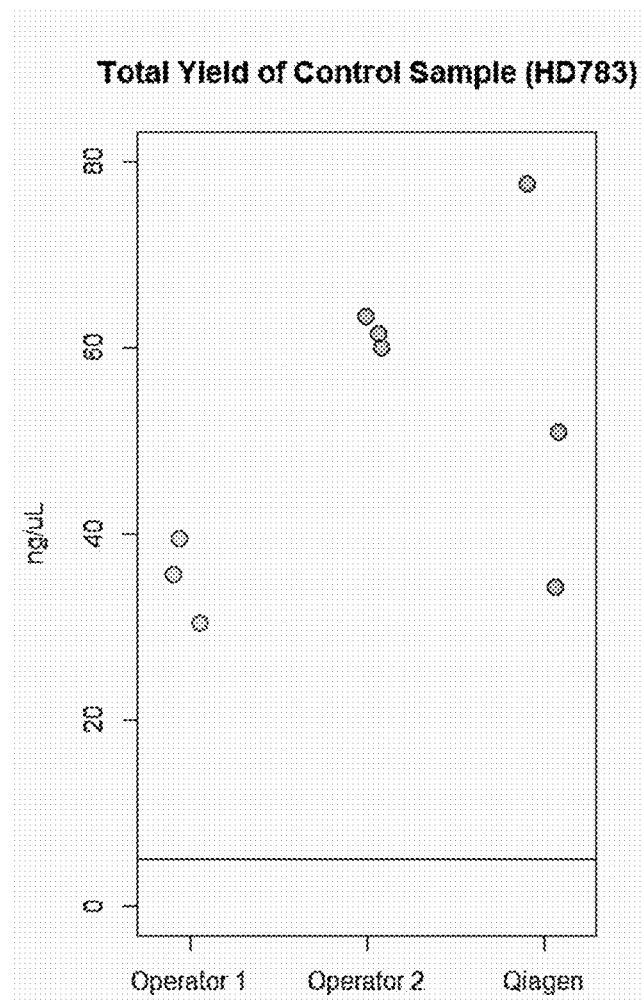
FIGS. 8A and 8B show the yield of mRNA from an FFPE reference sample using a reagent kit according to this invention.

FIGS. 8A and 8B show the results for a Fluidigm® reagent kit according to criteria (1), the total yield. For the HD783 control sample, the yield was 30 to 60 ng/µL.

Figures 8C, 8D:
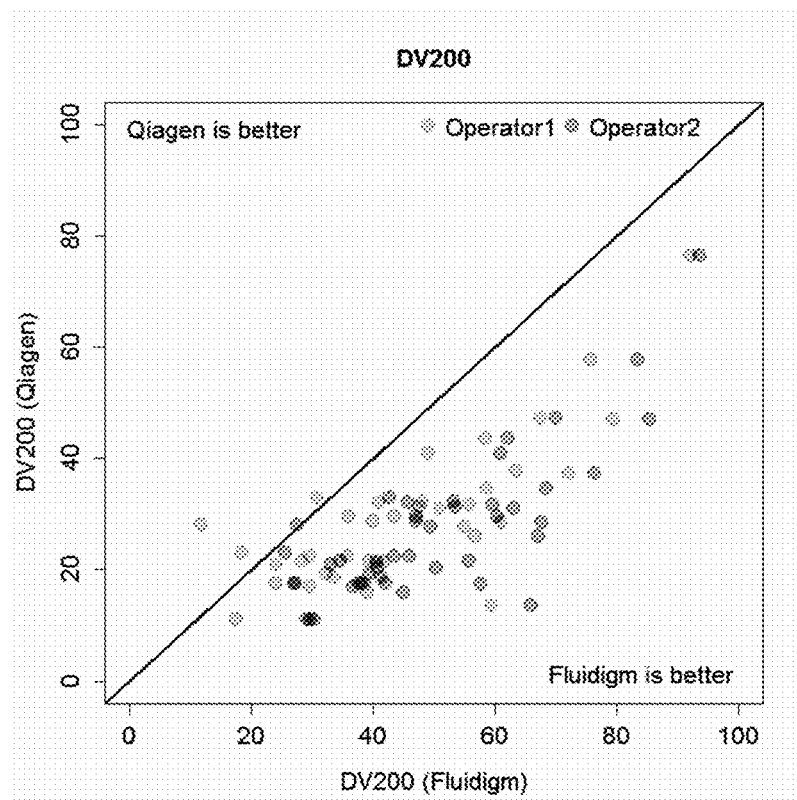
FIGS. 8C and 8D show the percentage of fragments over 200 base pairs in length (DV200).

FIGS. 8C and 8D compare results obtained from the Fluidigm® reagent kit (horizontal axis) is compared with the kit from Qiagen (vertical axis). Results are scored according to criteria (2), the percentage of fragments over 200 base pairs in length (DV200). Each point represents an independent FFPE sample tested with both kits (average of 2 or 3 replicates, depending on outlier removal, WSR p-value is not dependent on average values). The results show that RNA extraction with the Fluidigm kit yielded a higher proportion of larger RNA fragments vs. extraction with the Qiagen™ miRNeasy kit by both analysis methods (p<0.05).

Figures 8E, 8F:
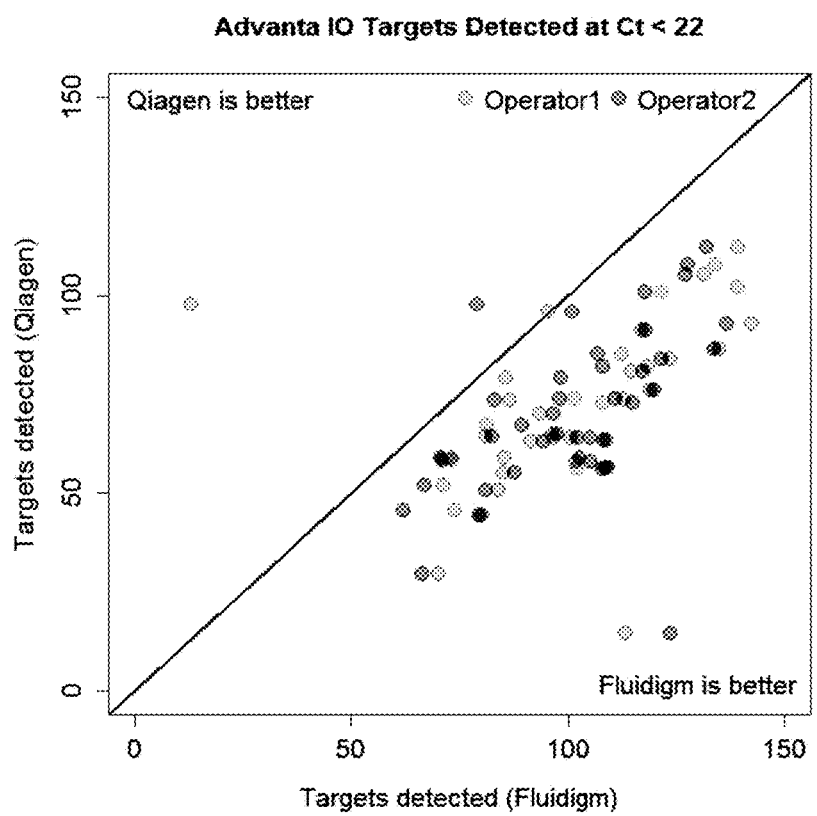
FIGS. 8E and 8F show the number of targets detected. Results for the test kit according to all three of these criteria were superior compared with results from a kit currently in commercial distribution.

FIGS. 8E and 8F show data obtained when the Fluidigm® reagent kit (horizontal axis) was compared with the kit from Qiagen (vertical axis) according to criteria (3), the number of targets detected. Each point represents an independent FFPE sample extraction comparisons (average of 3 replicates, 40+41 comparisons). RNA extraction with the Fluidigm kit detected more targets from the Advanta™ IO gene expression panel, compared with what was extracted using the Qiagen™ miRNeasy kit (p<0.05).

Figure 9A:
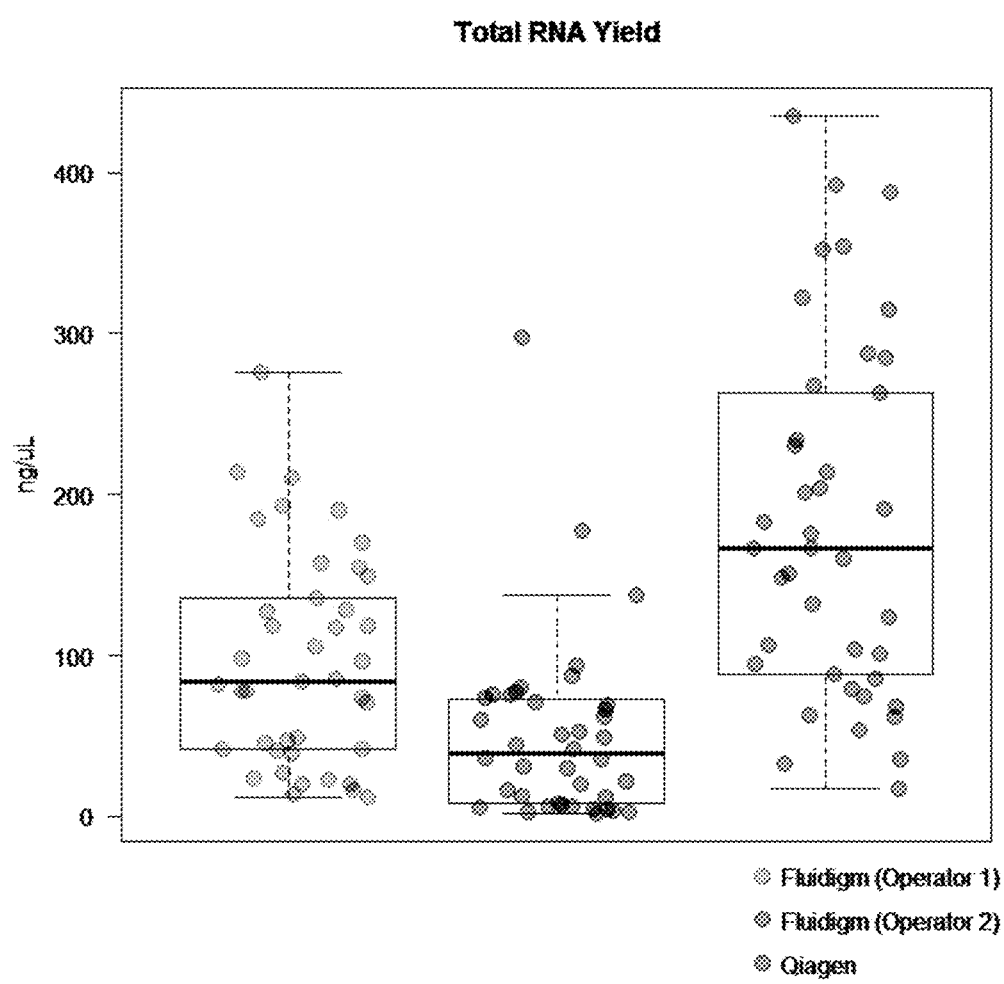
FIG. 9A compares the yield obtained using the Fluidigm® reagent kit with the yield obtained using a kit from Qiagen.

FIG. 9A compares the yield (criteria (1)) obtained using the Fluidigm® reagent kit with the yield obtained using the kit from Qiagen. The results show that extractions using the Qiagen kit result in higher overall RNA yield, as measured by the Qubit™ fluorimeter (Invitrogen). Despite higher overall yield, Qiagen RNA has lower performance with the Advanta™ 10 panel, and a lower proportion of fragments over 200 base pairs. Overall yield is not the most important criteria for FFPE extracted RNA. Both kits generate sufficient material for analysis by the Advanta™ 10 panel.

Figure 9C:
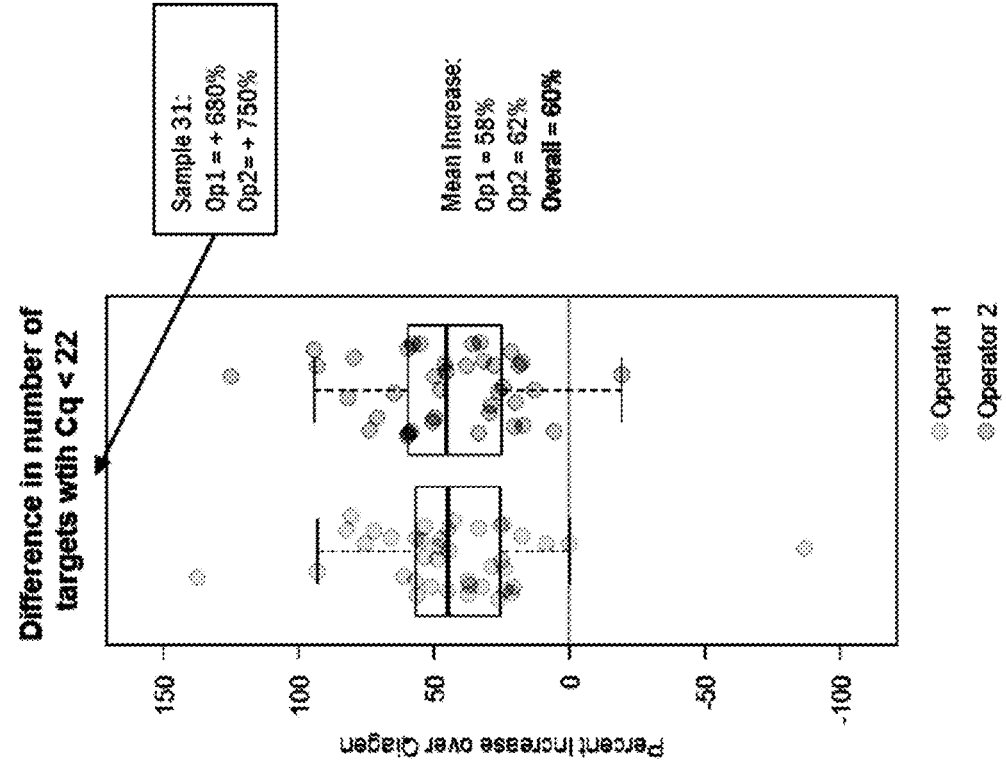
FIG. 9C shows that the number of targets identified by the Fluidigm kit had about a 45% improvement compared with the Qiagen kit.
Figure 9B:
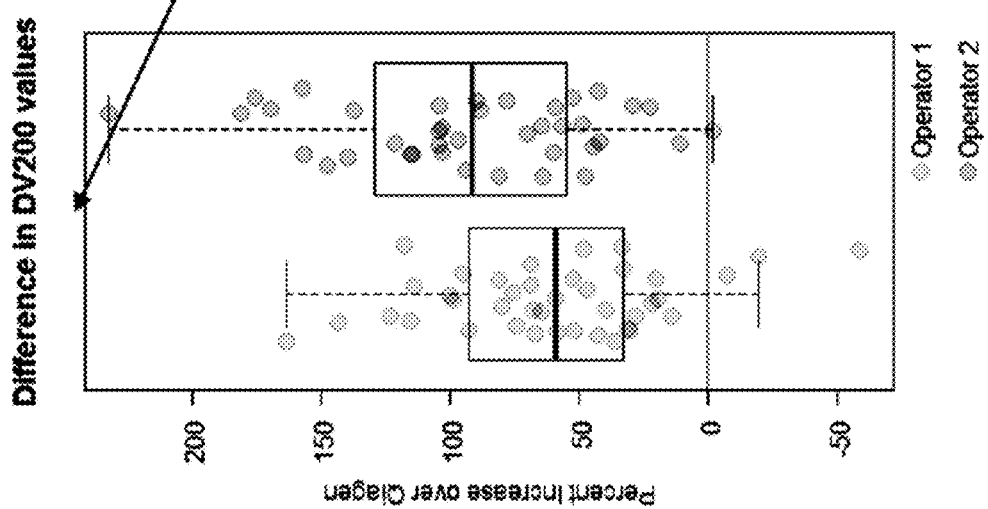
FIG. 9B shows that the Fluidigm kit had a 60% to 95% improvement in the DV200, the number of mRNA species detected that are 200 base pairs or more in length.

FIGS. 9B and 9C provide a visualization of performance enhancement with Fluidigm FFPE RNA extraction, in comparison with the Qiagen kit according to DV200 (criteria (2)) and the number of targets detected at Cq<22 (criteria (3)). Each point represents an independent FFPE sample (average of 3 replicates). FIG. 9B shows that depending on the operator, the Fluidigm kit had a 60% to 95% improvement in the DV values. FIG. 9C shows that the number of targets identified by the Fluidigm kit had about a 45% improvement, which was operator independent.

Thus, the Fluidigm® test kit passed the quality control analysis according to all three criteria. When assessed by criteria (2) and (3), results were improved to an extent that would substantially enhance expression analysis for purposes of research and/or clinical diagnosis.

While the foregoing invention has been described in some detail for purposes of clarity and understanding, it will be appreciated by those skilled in the relevant arts, once they have been made familiar with this disclosure, that various changes in form and detail can be made without departing from the true scope of the invention in the appended claims. The invention is therefore not to be limited to the exact components or details of methodology or construction set forth above. Except to the extent necessary or inherent in the processes themselves, no particular order to steps or stages of methods or processes described in this disclosure, including the Figures, is intended or implied. In many cases the order of process steps may be varied without changing the purpose, effect, or import of the methods described.

All publications and patent documents cited in this disclosure are incorporated herein by reference as if each such publication or document was specifically and individually indicated to be incorporated herein by reference. Citation of publications and patent documents (patents, published patent applications, and unpublished patent applications) is not intended as an admission that any such document is pertinent prior art, nor does it constitute any admission as to the contents or date of the same.

The invention claimed is:
1. A method of extracting nucleic acids from a wax-embedded biological sample, comprising:
(a) combining the biological sample with a wax-solubilizing organic solvent comprising a hydrocarbon of at least 10 carbon atoms to form a mixture; and
(b) adding an alcohol to the mixture;
whereby a precipitate is formed from the mixture that contains the nucleic acids after step (a) and before or after step (b); then
(c) separating the organic solvent and the alcohol from the precipitate;
(d) combining the precipitate with a lysis buffer so as to dissolve at least some of the precipitated nucleic acids from the sample that are in the precipitate to form a lysis solution;
(e) combining the lysis solution with a first aliquot of beads adapted to bind nucleic acids;
(f) recovering nucleic acids derived from the biological sample from the first aliquot of beads;
(g) treating the recovered nucleic acids in a buffer that contains DNase to remove deoxyribonucleic acids; and thereafter
(f) isolating RNA from the buffer containing DNase using a second aliquot of beads adapted to bind nucleic acids;
wherein the lysis buffer contains a protease and one or more detergents that include nonyl-phenoxypolyethoxylethanol (NP40), sodium dodecyl sulfate (SDS), or a combination of both NP40 and SDS.

2. The method of claim 1, wherein the one or more detergents include NP40.

3. The method of claim 1, wherein the one or more detergents include SDS at a concentration between 0.25% and 1% (w/v), wherein the concentration of the SDS is effective as an RNase inhibitor.

4. The method of claim 1, wherein the one or more detergents include both NP40 and SDS.

5. The method of claim 1, wherein the biological sample is a human tissue sample embedded in paraffin.

6. The method of claim 1, wherein the organic solvent comprises hexadecane.

7. The method of claim 1, wherein the alcohol is ethanol.

8. The method of claim 1, wherein the lysis buffer comprises proteinase K.

9. The method of claim 1, wherein the organic solvent is removed from the precipitate before the alcohol is added.

10. The method of claim 1, wherein the precipitate is dried before the lysis buffer is added.

11. The method of claim 1, further comprising determining nucleic acid sequences for nucleic acids or analyzing gene expression from nucleic acids recovered from the second aliquot of beads.

12. The method of claim 1 wherein the beads are magnetic particles coated with carboxyl groups in the form of succinic acid.

13. A method for improving the recovery of nucleic acids in a protocol for isolating nucleic acids from wax-embedded biological samples,
wherein the protocol comprises dissolving the wax-embedded sample in an organic solvent, extracting nucleic acids into an aqueous buffer, and isolating the nucleic acids from the aqueous buffer;
wherein the improvement comprises the following:
(1) using a saturated hydrocarbon comprising at least 10 carbon atoms as the organic solvent;
(2) causing the nucleic acids in the organic solvent to form a precipitate, which is then washed to remove the organic solvent and alcohol;
(3) including the non-ionic detergent nonyl-phenoxypolyethoxylethanol (NP40) and an RNA inhibitor in the aqueous buffer;
(4) treating the nucleic acids with DNase; and
(5) isolating the nucleic acids both before and after the DNase treatment using beads.

14. The method of claim 13, whereby the protocol is improved by one or both of the following criteria:
(1) a median percentage of fragments over 200 base pairs in length (DV200) of at least 40%; and
(2) a median number of unique mRNA transcripts detected at Cq<22 of at least 100.

15. The method of claim 13, wherein the RNase inhibitor is sodium dodecyl sulfate (SDS) and the saturated hydrocarbon is hexadecane.

16. A method of extracting ribonucleic acids (RNA) from a wax-embedded biological sample, comprising:
(a) combining the biological sample with a wax-solubilizing organic solvent to form a mixture;
(b) recovering from the mixture a precipitate that contains nucleic acids from the biological sample;
(c) washing the precipitate with a solution comprising an alcohol
(d) combining the washed precipitate with a lysis buffer that contains nonyl-phenoxypolyethoxylethanol (NP40), sodium dodecyl sulfate (SDS), and proteinase K so as to dissolve at least some of the nucleic acids from the sample that are in the precipitate to form a lysis solution;
(e) combining the lysis solution with a first aliquot of magnetic beads adapted to reversibly bind nucleic acids;
(f) recovering nucleic acids derived from the biological sample from the first aliquot of beads;
(g) treating the recovered nucleic acids in a buffer that contains DNase to remove deoxyribonucleic acids;
(h) combining the lysis solution containing the DNase treated nucleic acids with a second aliquot of magnetic beads adapted to reversibly bind nucleic acids; and
(i) recovering nucleic acids derived from the biological sample from the second aliquot of beads, thereby obtaining the ribonucleic acids (RNA) from the wax-embedded biological sample.

17. The method of claim 16, wherein the organic solvent comprises hexadecane and the alcohol is ethanol.

* * * * *